United States Patent
Saunier et al.

(10) Patent No.: US 6,733,540 B2
(45) Date of Patent: May 11, 2004

(54) USE OF 2-(SULPHONYLAMINO)PHENOLS AS COUPLERS IN OXIDATION COLORING

(75) Inventors: Jean-Baptiste Saunier, Paris (FR); Laurent Vidal, Paris (FR)

(73) Assignee: L'Oreal, Paris (FR)

( * ) Notice: Subject to any disclaimer, the term of this patent is extended or adjusted under 35 U.S.C. 154(b) by 204 days.

(21) Appl. No.: 09/987,434

(22) Filed: Nov. 14, 2001

(65) Prior Publication Data

US 2002/0100125 A1 Aug. 1, 2002

(30) Foreign Application Priority Data

Nov. 14, 2000 (FR) .............................. 00 14614

(51) Int. Cl.$^7$ ................................ A61K 7/13
(52) U.S. Cl. .............. 8/405; 8/401; 8/406; 8/407; 8/408; 8/409; 8/415; 8/424; 561/39
(58) Field of Search ............................ 8/401, 405, 406, 8/407, 408, 409, 415, 424; 562/39

(56) References Cited

U.S. PATENT DOCUMENTS

| 4,975,092 A | 12/1990 | Chan et al. | 8/408 |
| 6,537,329 B1 * | 3/2003 | Vidal et al. | 8/405 |

FOREIGN PATENT DOCUMENTS

| FR | 2 788 770 | 7/2000 |
| GB | 1 394 146 | 5/1975 |

* cited by examiner

*Primary Examiner*—Margaret Einsmann
*Assistant Examiner*—Eisa Elhilo
(74) *Attorney, Agent, or Firm*—Nixon & Vanderhye, P.C.

(57) ABSTRACT

The invention relates to the field of the oxidation dyeing of keratinous fibres and in particular of human keratinous fibers, such as the hair. The invention relates more particularly to the use of certain 2-(sulphonylamino)phenols of following formula (I) as coupler in combination with oxidation dye precursors for

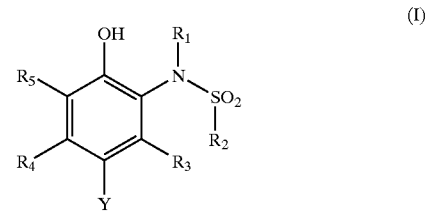

(I)

the oxidation dyeing of the fibers.

19 Claims, No Drawings

USE OF 2-(SULPHONYLAMINO)PHENOLS AS COUPLERS IN OXIDATION COLORING

The invention relates to the field of the oxidation dyeing of keratinous fibres and in particular of human keratinous fibres, such as the hair. The invention relates more particularly to the use of certain 2-(sulphonylamino)phenols in combination with oxidation dye precursors for the oxidation dyeing of fibres.

It is known to dye keratinous fibres and in particular human hair with dyeing compositions comprising oxidation dye precursors, in particular para-phenylenediamines, ortho- or para-aminophenols, or heterocyclic compounds, such as diaminopyrazole derivatives, generally known as oxidation bases. Oxidation dye precursors or oxidation bases are colourless or weakly coloured compounds which, in combination with oxidizing substances, can give rise by an oxidative coupling process to coloured and colouring compounds.

It is also known that the shades obtained with these oxidation bases can be varied by combining them with couplers or colouring modifiers, the latter being chosen in particular from aromatic meta-diamines, meta-aminophenols, meta-diphenols, non-cationic naphthols or certain heterocyclic compounds, such as, for example, indole couplers.

The variety of the molecules employed as oxidation bases and couplers makes it possible to obtain a rich palette of colours.

The <<permanent>> colouring obtained by virtue of these oxidation dyes has, however, to satisfy a certain number of requirements. Thus, it must be without disadvantage toxicologically, it must make it possible to obtain shades in the desired intensity and it must behave well in the face of external agents (light, bad weather, washing, permanent waving, perspiration or rubbing).

The dyes must also make it possible to cover white hair and, finally, be as unselective as possible, that is to say make it possible to obtain the least possible differences in colouring along the same keratinous fibre, this being because the latter can be sensitized (i.e. damaged) to a varying degree between its tip and its root.

Provision has already been made, in particular in Patent Application BE 803 712, for oxidation dyeing compositions comprising nitrated 2-(sulphonylamino)phenols as direct yellow dye or as yellow couplers, in combination with oxidation bases conventionally used in oxidation dyeing, such as, for example, para-phenylenediamine, para-toluylenediamine, para-dimethylaminoaniline, para-aminophenol or para-diaminoanisole. Such compositions are not, however, always satisfactory, in particular from the viewpoint of the power and the chromaticity of the colourings obtained.

The Applicant Company has now just discovered, in a completely unexpected and surprising way, that it is possible to obtain novel dyes, which dyes are capable of resulting in powerful colourings in shades varying from red to blue which are particularly chromatic and bright, which are not very selective and which exhibit excellent properties of resistance to the various attacks which keratinous fibres may be subjected to, by combining at least one oxidation base and at least one coupler chosen from certain 2-(sulphonylamino) phenols.

A first subject-matter of the invention is therefore a composition for the oxidation dyeing of keratinous fibres and in particular of human keratinous fibres, such as the hair, comprising, in a medium appropriate for the dyeing of the said fibres:

at least one oxidation base;
and at least one coupler chosen from the compounds of following formula (I) and/or their addition salts with an acid:

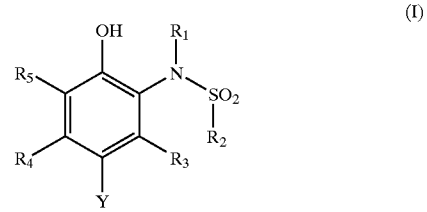

(I)

in which:

$R_1$ represents a hydrogen atom or a linear or branched radical comprising from 1 to 15 carbon atoms (it being possible for the branching or branchings to form one or more carbonaceous rings comprising from 3 to 7 ring members) which can comprise one or more double bonds and/or one or more triple bonds (the said double bonds optionally resulting in aromatic groups) and one or more carbon atoms of which can be replaced by an oxygen, nitrogen or sulphur atom or by an $SO_2$ group and the carbon atoms of which can, independently of one another, be substituted by one or more halogen atoms, the said $R_1$ radical comprising neither peroxide bonds nor diazo, nitro and nitroso radicals;

$R_2$ represents a hydrogen atom or a linear or branched radical comprising from 1 to 20 carbon atoms (it being possible for the branching or branchings to form one or more carbonaceous rings comprising from 3 to 7 ring members) which can comprise one or more double bonds and/or one or more triple bonds (the said double bonds optionally resulting in aromatic groups) and one or more carbon atoms of which can be replaced by an oxygen, nitrogen or sulphur atom or by an $SO_2$ group and the carbon atoms of which can, independently of one another, be substituted by one or more halogen atoms, the said $R_2$ radical comprising neither peroxide bonds nor diazo, nitro and nitroso radicals;

$R_3$, $R_4$ and $R_5$, which are identical or different, represent a hydrogen or halogen atom or a linear or branched radical comprising from 1 to 20 carbon atoms (it then being possible for the branching or branchings to form one or more rings comprising from 3 to 7 ring members) which can comprise one or more double bonds and/or one or more triple bonds (the said double bonds optionally resulting in aromatic groups) and one or more carbon atoms of which can be replaced by an oxygen, nitrogen or sulphur atom or by an $SO_2$ group and the carbon atoms of which can, independently of one another, be substituted by one or more halogen atoms, the said radical comprising neither peroxide bonds nor diazo, nitro and nitroso radicals and it being understood that $R_5$ cannot represent a hydroxyl, thio or amino radical and it being understood that the $R_3$, $R_4$ and $R_5$ radicals cannot be connected to the benzene ring of the formula (I) via an —NH—NH— bond;

Y represents a hydrogen or halogen atom; an —$OR_6$, —$SR_6$ or —NH—$SO_2R$, group in which $R_6$ represents a linear or branched $C_1$–$C_6$ alkyl radical (it then being possible for the branching or branchings to form one or more rings comprising from 3 to 6 ring members), optionally substituted by one or more radicals chosen from the group: halogen, hydroxyl, $C_1$–$C_4$ alkoxy, amino or $C_1$–$C_4$ aminoalkyl; a phenyl radical, optionally substituted by one or two radicals chosen from the group: $C_1$–$C_4$ alkyl, trifluoromethyl, carboxyl, $C_1$–$C_4$ alkoxycarbonyl, halogen, hydroxyl, $C_1$–$C_4$ alkoxy, amino or $C_1$–$C_4$ aminoalkyl; or a benzyl radical.

As indicated above, the oxidation dyeing composition comprising the compound or compounds of formula (I) in accordance with the invention makes it possible to obtain powerful colourings in shades varying from red to blue which furthermore exhibit a noteworthy persistence towards the various treatments which keratinous fibres may be subjected to. These properties are particularly noteworthy especially as regards the resistance of the colourings obtained with respect to the action of bad weather, washing, permanent waving and perspiration.

Another subject-matter of the invention is a process for the oxidation dyeing of keratinous fibres employing this dyeing composition.

According to the invention, when it is indicated that one or more of the carbon atoms of the $R_1$ to $R_5$ radical or radicals can be replaced by an oxygen, nitrogen or sulphur atom or by an $SO_2$ group and/or that the said $R_1$ to $R_5$ radicals can comprise one or more double bonds and/or one or more triple bonds, this means that it is possible, by way of example, to carry out the following

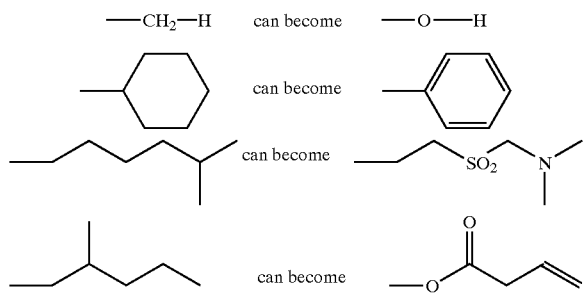

conversions:

According to the invention, preferably denotes a hydrogen atom or an $A_1$, $A_2$, $A_3$, $A_4$ or $A_5$ group as defined is below.

According to the invention, the term <<A group>> is understood to mean a linear or branched $C_1$–$C_6$ hydrocarbonaceous radical which can carry one or two double bonds or one triple bond, which may or may not be substituted by a group chosen from an $A_2$ group, an $A_4$ group or an $A_5$ group, which may or may not be substituted by one or two identical or different groups chosen from the N—($C_1$–$C_3$) alkylamino, N—($C_1$–$C_3$) alkyl-N—($C_1$–$C_3$) alkylamino, ($C_1$–$C_6$)alkoxy, oxo, alkoxycarbonyl, acyloxy, amido, acylamino, ureyl, sulphoxy, sulphonyl, sulphonamido, sulphonylamino, bromo, cyano or carboxyl groups, and which may or may not be substituted by one or more hydroxyl, fluoro or chloro groups.

The term <<$A_2$ group>> is understood to mean an aromatic group of phenyl, benzyl or naphthyl type which may or may not be substituted by one to three identical or different groups chosen from the methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups.

The term <<$A_3$ group>> is understood to mean heteroaromatic groups chosen from the furanyl, thiophenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolinyl, benzimidazolyl or benzopyrimidyl groups, optionally substituted by 1 to 3 radicals chosen from linear or branched $C_1$–$C_4$ alkyl, $C_1$–$C_4$ (poly)hydroxyalkyl, carboxyl, alkoxycarbonyl, halogen, amido, amino or hydroxyl.

The term <<$A_4$ group>> is understood to mean a $C_3$–$C_7$ cycloalkyl or a norbornanyl radical which can optionally carry a double bond and which is optionally substituted by 1 or 2 radicals defined by linear or branched $C_1$–$C_4$ alkyl, $C_1$–$C_4$ (poly)hydroxyalkyl, carboxyl, alkoxycarbonyl, halogen, amido, amino or hydroxyl.

The term <<$A_5$ group>> is understood to mean a heterocycle defined by dihydrofuranyl, tetrahydrofuranyl, butyrolactoneyl, dihydrothiophenyl, tetrahydrothiophenyl, tetrahydrothiophenoneyl, iminothiolanyl, dihydropyrrolyl, pyrrolidinyl, pyrrolidinoneyl, imidazolidinoneyl, imidazolidinethioneyl, oxazolidinyl, oxazolidinoneyl, oxazolanethioneyl, thiazolidinyl, isothiazoloneyl, mercaptothiazolinyl, pyrazolidinoneyl, iminothiolanyl, dioxolanyl, pentalactoneyl, dioxanyl, dihydropyridinyl, piperidinyl, pentalactamyl, morpholinyl, pyrazoli(di)nyl, pyrimi(di)nyl, pyrazinyl, piperazinyl and azepinyl.

Among these substituents, $R_1$ preferably represents a hydrogen atom, a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphtho-methyl radical; or a 2-hydroxyethyl, 2-methoxyethyl or 2-ethoxyethyl group.

More preferably still, $R_1$ represents a hydrogen atom or a methyl radical.

According to the invention, $R_2$ preferably denotes a hydrogen atom, an amino group or an $A_1$, $A_2$, $A_3$, $A_4$ or $A_5$ group as defined above, optionally separated from the sulphur (in the 8 position) of the sulphonamide functional group of the compound of formula (T) by an —NH— or —N—($C_1$–$C_3$)alkyl-group.

Among these substituents, $R_2$ preferably denotes a radical chosen from the group (G1) consisting of the methyl, trifluoromethyl, ethyl, 2-chloroethyl, propyl, 3-chloropropyl, isopropyl, butyl, phenyl, ethoxy, amino and dimethylamino radicals.

More preferably still, $R_2$ represents a methyl, ethyl, phenyl or dimethylamino radical.

According to the invention, $R_3$ and $R_4$, which are identical or different, preferably denote a hydrogen or halogen atom; a hydroxyl or amino group; an $A_1$, $A_4$ or $A_5$ group as defined above; or an $A_1$, $A_2$, $A_3$, $A_4$ or $A_5$ group as defined above separated from the phenol nucleus of the formula (I) by an oxygen atom or by an —NH—, —N—($C_1$–$C_3$)alkyl-, —O(CO)—, —NH(CO)—, —N—($C_1$–$C_3$)alkyl(CO)—, —NH[C=NH]—, —NH(CO)NH—, —NH (CO)N—($C_1$–$C_3$)alkyl-, —NH(CO)O—, —NHSO$_2$—, —NHSO$_2$NH— or —NHSO$_2$N—($C_1$–$C_3$)alkyl-group.

Among these substituents, $R_3$ preferably represents a hydrogen or chlorine atom; a methyl, hydroxymethyl, methoxymethyl, 1-hydroxyethyl, aminomethyl or methylaminomethyl radical; a hydroxyl, methoxy or acetoxy radical; an amino, methylamino or 2-hydroxyethylamino radical; an —NH(CO)$R_7$ group in which $R_7$ represents one of the radicals listed in the group (G2) consisting of the methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-s-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2, 2,3,3,4,4-octafluorobutyl, nonafluorobutyl, chloromethyl, chloroethyl, 1,1-dimethyl-2-chloroethyl, 1,2-di-chloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or an —NHSO$_2$R$_8$ group in which R$_8$ represents one of the radicals listed in the group (GI) as defined above.

More preferably still, R$_3$ represents a hydrogen atom; a methyl, hydroxymethyl, aminomethyl, hydroxyl, methoxy, amino or methylamino radical; an —NH(CO)R$_8$ group in which R$_8$ is chosen from the group (G3) consisting of the methyl, ethyl, propyl, allyl, phenyl, tetrahydrofuran-2-yl, furan-2-yl, thiophen-2-yl, pyridinyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radicals; or a methanesulphonylamino, ethanesulphonylamino, benzenesulphonylamino or dimethylaminosulphonylamino group.

Among these substituents, R$_4$ preferably represents a hydrogen or chlorine atom; a methyl, ethyl, hydroxymethyl, methoxymethyl, aminomethyl or methylaminomethyl radical; a hydroxyl, methoxy, acetoxy, amino, methylamino, N-piperidino or N-morpholino group; an —NH(CO)R$_{10}$ group in which R$_{10}$ represents one of the radicals listed in the group (G2) defined above; or an —NHSO$_2$R$_{11}$, group in which R$_{11}$ represents one of the radicals listed in the group (G1) defined above.

More preferably still, R$_4$ represents a hydrogen or chlorine atom; a methyl, hydroxymethyl, aminomethyl, hydroxyl, methoxy, amino or methylamino radical; an —NH(CO)R$_{12}$ group in which R$_{12}$ represents one of the radicals listed in the group (G3) defined above; or a methanesulphonylamino, ethanesulphonylamino, benzenesulphonylamino or dimethylaminosulphonylamino group.

According to the invention, R$_5$ is preferably chosen from a hydrogen or halogen atom; an A$_1$, A$_4$ or A$_5$ group as defined above; or an A$_1$, A$_2$, A$_3$, A$_4$ or A$_5$ group as defined above separated from the phenyl nucleus of the compounds of formula (I) by an oxygen or sulphur atom or by an —NH—, —N—(C$_1$–C$_3$)alkyl-, —NH(CO)—, —N—(C$_1$–C$_3$)alkyl(CO)—, —NH[C=NH]—, —NH(CO)NH—, —NH(CO)N—(C$_1$–C$_3$)alkyl- or —NH(CO)O— group.

Among these substituents, R$_5$ preferably represents a hydrogen, chlorine, fluorine or bromine atom; a methyl, trifluoromethyl, allyl, hydroxymethyl, methoxymethyl, 1-hydroxyethyl, aminomethyl, methylaminomethyl, methoxy, acetoxy or methylamino radical; an —NH(CO)R$_{13}$ group in which R$_{13}$ represents one of the radicals listed in the group (G2) defined above; or an —NHSO$_2$R$_{14}$ group in which R$_{14}$ represents one of the radicals listed in the group (G1) defined above.

More preferably still, R$_5$ represents a hydrogen, chlorine or fluorine atom; a methyl, hydroxymethyl, aminomethyl, methoxy or methylamino group; an —NH(CO)R$_{15}$ group in which R$_{15}$ represents one of the radicals listed in the group (G3) defined above; or a methanesulphonylamino, ethanesulphonylamino, benzenesulphonylamino or dimethylaminosulphonylamino group.

According to the invention, Y is preferably chosen from a hydrogen, chlorine, fluorine or bromine atom; a methoxy, ethoxy, propoxy, benzyloxy or phenoxy group; or an —OCH$_2$CH$_2$OCH$_3$, —OCH$_2$CH$_2$OCH$_3$, —OCH$_2$CH$_2$N(CH$_3$)$_2$, —OCH$_2$(CO)OH, —OCH$_{12}$(CO)OCH$_3$, —OCH$_2$(CO)OC$_2$H$_5$, —SCH$_2$CH$_2$CO$_2$H or —NHSO$_2$CH$_3$ group.

More preferably still, Y is chosen from a hydrogen or chlorine atom or a methoxy, —OCH$_2$(CO)OC or —OCH$_2$(CO)OCH$_3$ group.

Among the compounds of formula (I), preference is particularly given to those in which:
i) R$_1$ represents a hydrogen atom;
R$_2$ represents a methyl, ethyl, phenyl or dimethylamino radical;
R$_3$ represents a hydroxyl, amino or methylamino radical; an —NH(CO)R$_{15}$ group in which RAS represents a radical chosen from the group (G4) consisting of the methyl, methoxymethyl, 2-carboxyethyl, methoxy, amino, 15 ethylamino and 1-pyrrolidinyl radicals; methanesulphonylamino, ethanesulphonylamino and dimethylaminosulphonylamino;
R$_4$ represents a hydrogen or chlorine atom or a methyl group;
R$_5$ represents a hydrogen, chlorine or fluorine atom or a methyl group;
Y represents a hydrogen or chlorine atom or a methoxy or —OCH$_2$(CO)OCH$_3$ group;

ii) $R_1$ represents a hydrogen atom;
   $R_2$ represents a methyl, ethyl, phenyl or dimethylamino radical;
   $R_3$ represents a hydrogen atom or a methyl radical;
   $R_4$ represents a hydroxyl, amino, methylamino or —NH(CO)$R_{17}$ group in which $R_{17}$ represents one of the radicals listed in the group (G4) defined above; or a methanesulphonylamino, ethanesulphonylamino or dimethylaminosulphonylamino group;
   $R_5$ represents a hydrogen, chlorine or fluorine atom or a methyl, methoxy or methylamino group;
   Y represents a hydrogen or chlorine atom or a methoxy or —OCH$_2$(CO)OCH$_3$ group;
iii) $R_1$ represents a hydrogen atom;
   $R_2$ represents a methyl, ethyl, phenyl or dimethylamino radical;
   $R_3$ represents a hydrogen atom or a methyl radical;
   $R_4$ represents a hydrogen or chlorine atom or a methyl, methoxy or methylamino radical;
   $R_5$ represents a methylamino or —NH(CO)$R_{18}$ group in which $R_{18}$ represents one of the radicals listed in the group (G4) defined above; or a methanesulphonylamino, ethanesulphonylamino or dimethylaminosulphonylamino group;
   Y represents a hydrogen or chlorine atom or a methoxy or —OCH$_2$(CO)OCH$_3$ group;
iv) $R_1$ represents a hydrogen atom;
   $R_2$ represents a methyl, ethyl, phenyl or dimethylamino radical;
   $R_3$ represents a hydrogen atom or a methyl radical;
   $R_4$ represents a hydrogen or chlorine atom or a methyl radical;
   $R_5$ represents a hydrogen, chlorine or fluorine atom or a methyl radical;
   Y represents a hydrogen or chlorine atom or a methoxy or —OCH$_2$(CO)OCH$_3$ group.

Mention may be made, among the compounds of formula (I) above, of:
N-(2-hydroxyphenyl)methanesulphonamide;
N-(2-hydroxy-4-methylphenyl)methanesulphonamide;
N-(2-hydroxy-4-aminophenyl)methanesulphonamide;
N-(2-hydroxy-4-(acetylamino)phenyl) methanesulphonamide;
N-(2-hydroxy-4-(methoxycarbonylamino)phenyl) methanesulphonamide;
N-(2-hydroxy-5-chlorophenyl)methanesulphonamide;
N-(2-hydroxy-4-methyl-5-chlorophenyl) methanesulphonamide;
N-(2-hydroxy-4-amino-5-chlorophenyl) methanesulphonamide;
N-(2-hydroxy-4-acetylamino-5-chlorophenyl) methanesulphonamide;
N-(2-hydroxy-4-methoxycarbonylamino-5-chlorophenyl) methanesulphonamide;
N-(2-hydroxy-5-methoxyphenyl)methanesulphonamide;
N-(2-hydroxy-4-methyl-5-methoxyphenyl) methanesulphonamide;
N-(2-hydroxy-4-amino-5-methoxyphenyl) methanesulphonamide;
N-(2-hydroxy-4-acetylamino-5-methoxyphenyl) methanesulphonamide;
N-(2-hydroxy-4-methoxycarbonylamino-5-methoxyphenyl) methanesulphonamide; N-(2-hydroxy-6-aminophenyl) methanesulphonamide;
N-(2-hydroxy-6-(acetylamino)phenyl) methanesulphonamide;
N-(2-hydroxy-4,6-diaminophenyl)methanesulphonamide;
N-(2-hydroxy-4-acetylamino-6-aminophenyl) methanesulphonamide;
N-(2-hydroxy-3,5-dichloro-4-methylphenyl) methanesulphonamide;
N-(2-hydroxy-3,5-dichloro-4-aminophenyl) methanesulphonamide;
N-(2-hydroxy-3,5-dichloro-4-(acetylamino)phenyl) methanesulphonamide;
N-(2-hydroxy-3,5-dichloro-4-(methoxycarbonylamino) phenyl)methanesulphonamide;
N-(2-hydroxy-3-(methanesulphonylamino)phenyl) methanesulphonamide;
N-(2-hydroxyphenyl)benzenesulphonamide;
N-(2-hydroxy-4-methylphenyl)benzenesulphonamide;
N-(2-hydroxy-4-aminophenyl)benzenesulphonamide;
N-(2-hydroxy-4-(acetylamino)phenyl) benzenesulphonamide;
N-(2-hydroxy-4-(methoxycarbonylamino)phenyl) benzenesulphonamide;
N-(2-hydroxy-5-chlorophenyl)benzenesulphonamide;
N-(2-hydroxy-4-methyl-5-chlorophenyl) benzenesulphonamide;
N-(2-hydroxy-4-amino-5-chlorophenyl) benzenesulphonamide;
N-(2-hydroxy-4-acetylamino-5-chlorophenyl) benzenesulphonamide;
N-(2-hydroxy-4-methoxycarbonylamino-5-chlorophenyl) benzenesulphonamide;
N-(2-hydroxy-5-methoxyphenyl)benzenesulphonamide;
N-(2-hydroxy-4-methyl-5-methoxyphenyl) benzenesulphonamide;
N-(2-hydroxy-4-amino-5-methoxyphenyl) benzenesulphonamide;
N-(2-hydroxy-4-acetylamino-5-methoxyphenyl) benzenesulphonamide;
N-(2-hydroxy-4-methoxycarbonylamino-5-methoxyphenyl) benzenesulphonamide;
N-(2-hydroxy-6-aminophenyl)benzenesulphonamide;
N-(2-hydroxy-6-(acetylamino)phenyl) benzenesulphonamide;
N-(2-hydroxy-4,6-diaminophenyl)benzenesulphonamide;
N-(2-hydroxy-4-acetylamino-6-aminophenyl) benzenesulphonamide;
N-(2-hydroxy-3,5-dichloro-4-methylphenyl) benzenesulphonamide;
N-(2-hydroxy-3,5-dichloro-4-aminophenyl) benzenesulphonamide;
N-(2-hydroxy-3,5-dichloro-4-(acetylamino)phenyl) benzenesulphonamide;
N-(2-hydroxy-3,5-dichloro-4-(methoxycarbonylamino) phenyl)benzenesulphonamide;
N-(2-hydroxy-3-(benzenesulphonylamino)phenyl) benzenesulphonamide;
and their addition salts with an acid.

The compounds of formula (I) in accordance with the invention can be prepared according to methods well known in the state of the art and disclosed, for example, in patent applications or patents EP 0 718 297, EP 0 576 172, U.S. Pat. No. 4,250,246, DE 2 906 526, U.S. Pat. Nos. 4,200,466, 4,004,028, 3,920,444, DE 2 156 480 and U.S. Pat. No. 3,660,487.

The compound or compounds of formula (I) in accordance with the invention and/or the addition salt or their addition salts with an acid preferably represent from 0.0005 to 12% by weight approximately of the total weight of the dyeing composition and more preferably still from 0.005 to 6% by weight approximately of this weight.

The oxidation dyeing composition according to the invention comprises one or more oxidation bases which are preferably chosen from the oxidation bases conventionally used in oxidation dyeing and among which may in particular be mentioned para-phenylenediamines, bisphenylalkylenediamines, para-aminophenols, ortho-aminophenols and heterocyclic bases.

Mention may more particularly be made, among the para-phenylenediamines, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine N-(β-hydroxypropyl)-para-phenylene-diamine, 2-hydroxymethyl-para-phenylenediamine, N,N-dimethyl-3-methyl-para-phenylenediamine, N,N-(ethyl, β-hydroxyethyl)-para-phenylenediamine, N-(β,β-dihydroxypropyl)-para-phenylenediamine, N-(4'-aminophenyl)-para-phenylenediamine, N-phenyl-para-phenylenediamine, 2-_-hydroxyethyloxy-para-phenylenediamine, 2-β-acetyl-aminoethyloxy-para-phenylenediamine, N-(β-methoxyethyl)-para-phenylenediamine and their addition salts with an acid.

Preference is very particularly given, among the para-phenylenediamines mentioned above, to para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine and their addition salts with an acid.

Mention may more particularly be made, among the bis-phenylalkylenediamines, by way of example, of N,N'-bis-(β-hydroxyethyl)-N,N'-bis(4'-aminophenyl)-1,3-diaminoprodanol, N,N'-bis(β-hydroxyethyl)-N,N'-bis(4;-aminophenyl)ethylenediamine, N,N'-bis(4-aminophenyl)tetramethylenediamine, N,N'-bis (β-hydroxyethyl)-N,N'-bis-(4-aminophenyl)tetramethylenediamine, N,N'-bis-(4-(methyl)aminophenyl)tetramethylenediamine, N,N'-diethyl-N,N'-bis(4'-amino-3'-methylphenyl)ethylenediamine, 1,8-bis(2,5-diaminophenoxy)-3,5-dioxaoctane and their addition salts with an acid, Mention may more particularly be made, among the para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their addition salts with an acid.

Mention may more particularly be made, among the ortho-aminophenols, by way of example, of 2-aminophenol, 2-amino-5-methylphenol, 2-amino-6-methylphenol, 5-acetamido-2-aminophenol and their addition salts with an acid.

Mention may more particularly be made, among the heterocyclic bases, by way of example, of pyridine derivatives, pyrimidine derivatives and pyrazole derivatives.

Mention may more particularly be made, among the pyridine derivatives, of the compounds disclosed, for example, in Patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine and their addition salts with an acid.

Mention may more particularly be made, among the pyrimidine derivatives, of the compounds disclosed, for example, in German Patent DE 2 359 399 or Japanese Patents JP 88-169 571 and JP 91-10659 or Patent Application WO 96/15765, such as 2,4,5,6-tetraaminopyrimidine, 4-hydroxy-2,5,6-triaminopyrimidine, 2-hydroxy-4,5,$^6$-triaminopyrimidine, 2,4-dihydroxy-5,6-di-aminopyrimidine or 2,5,6-triaminopyrimidine.

Mention may more particularly be made, among the pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methypyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-di-amino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-di-amino-4(β-hydroxyethyl)amino-1-methylpyrazole and their addition salts with an acid.

The oxidation base or bases preferably represent from 0.0005 to 12% by weight approximately of the total weight of the dyeing composition and more preferably still from 0.005 to 6% by weight approximately of this weight.

The dyeing composition in accordance with the invention can also include, in addition to the compound or compounds of formula (I) above, one or more additional couplers which can be chosen from the couplers conventionally used in oxidation dyeing and among which may in particular be mentioned meta-phenylenediamines, meta-aminophenols, meta-diphenols and heterocyclic couplers, such as, for example, indole derivatives, indoline derivatives, pyridine derivatives and pyrazolones, and their addition salts with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(_-hydroxyethylamino)-1-methoxybenzene, 1,3-diaminobenzene, 1,3-bis(2,4-diaminophenoxy)propane, sesamol, β-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one and their addition salts with an acid.

When they are present, these additional couplers preferably represent from 0.0001 to 10% by weight approximately of the total weight of the dyeing composition and more preferably still from 0.005 to 5% by weight approximately of this weight.

Generally, the addition salts with an acid which can be used in the context of the dyeing compositions of the invention (compounds of formula (I), oxidation bases and additional couplers) are chosen in particular from hydrochlorides, hydrobromides, sulphates, citrates, succinates, tartrates, lactates and acetates.

The medium appropriate for dyeing (or vehicle) is generally composed of water or of a mixture of water and of at least one organic solvent, in order to dissolve the compounds which would not be sufficiently soluble in water. Mention may be made, For example, as organic solvent, of lower $C_1$–$C_4$ alkanols, such as ethanol and isopropanol; glycerol; glycols and glycol ethers, such as 2-butoxyethanol, propylene glycol, propylene glycol monomethyl ether, diethylene glycol monoethyl ether and diethylene glycol monomethyl ether; and aromatic alcohols such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition in accordance with the invention is generally between 3 and 12 approximately and preferably between 5 and 11 approximately. It can be adjusted to the desired value by means of acidifying or basifying agents commonly used in dyeing keratinous fibres.

Mention may be made, among acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among basifying agents, by way of example, of aqueous ammonia, akaline carbonates, alkanolamines, such as mono-, di- and triethanolamines, and their derivatives, sodium hydroxide, potassium hydroxide

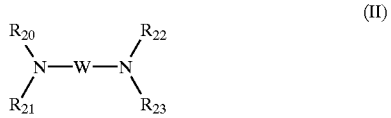

(II)

and the compounds of following formula (II):
in which W is a propylene residue which is or is not substituted by a hydroxyl group or a $C_1$–$C_6$ alkyl radical and $R_{20}$, $R_{21}$, $R_{22}$ and $R_{23}$, which are identical or different, represent a hydrogen atom or a $C_1$–$C_6$ alkyl or $C_1$–$C_6$ hydroxyalkyl radical.

The oxidation dyeing compositions in accordance with the invention can also include at least one direct dye, in particular for modifying the shades or enriching them with highlights.

The dyeing composition in accordance with the invention can also include various adjuvants conventionally used in hair dyeing compositions, such as anionic, cationic, nonionic, amphoteric or zwitterionic surface-active agents or their mixtures, anionic, cationic, nonionic, amphoteric or zwitterionic polymers or their mixtures, inorganic or organic thickening agents, antioxidizing agents, penetration agents, sequestering agents, fragrances, buffers, dispersing agents, conditioning agents, such as, for example, volatile or non-volatile and modified or unmodified silicones, film-forming agents, ceramides, preserving agents or opacifying agents.

Of course, a person skilled in the art will take care to choose this or these optional additional compound or compounds so that the advantageous properties intrinsically attached to the oxidation dyeing composition in accordance with the invention are not, or not substantially, detrimentally affected by the envisaged addition or additions.

The dyeing composition according to the invention can be provided in various forms, such as in the form of liquids, creams or gels or in any other form appropriate for carrying out dyeing of keratinous fibres and in particular human hair.

Another subject-matter of the invention is a process for the oxidation dyeing of keratinous fibres and in particular human keratinous fibres, such as the hair, employing the dyeing composition as defined above.

According to this process, at least one dyeing composition as defined above is applied to the fibres, the colour being developed at acidic, neutral or alkaline pH using an oxidizing agent which is added only at the time of use to the dyeing composition or which is present in an oxidizing composition applied simultaneously or sequentially.

According to a preferred embodiment of the dyeing process of the invention, the dyeing composition described above is preferably mixed, at the time of use, with an oxidizing composition comprising, in a medium appropriate for dyeing, at least one oxidizing agent present in an amount sufficient to develop a colouring. The mixture obtained is subsequently applied to the keratinous fibres and is left to stand for 3 to SO minutes approximately, preferably 5 to 30 minutes approximately, after which the hair is rinsed, washed with shampoo, rinsed again and dried.

The oxidizing agent can be chosen from oxidizing agents conventionally used for the oxidation dyeing of keratinous fibres and among which may be mentioned hydrogen peroxide, urea hydrogen peroxide, alkali metal bromates, persalts, such as perborates and persulphates, and enzymes, such as peroxidases, laccases, tyrosinases and oxidoreductases, among which may in particular be mentioned pyranose oxidases, glucose oxidases, glycerol oxidases, lactate oxidases, pyruvate oxidases and uricases.

The pH of the oxidizing composition including the oxidizing agent as defined above is such that, after mixing with the dyeing composition, the pH of the resulting composition applied to keratinous fibres preferably varies between 3 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to keratinous fibres can be provided in various forms, such as in the form of liquids, creams or gels or in any other form appropriate for carrying out dyeing of keratinous fibres and in particular of human hair.

A final subject-matter of the invention is a multi-compartment device or dyeing kit or any other packaging system with several compartments, a first compartment of which includes the dyeing composition as defined above and a second compartment of which includes the oxidizing composition as defined above. These devices can be equipped with a means allowing the desired mixture to be delivered to the hair, such as the devices disclosed in Patent FR-2 586 913 on behalf of the Applicant Company.

The examples which follow are intended to illustrate the invention without, however, limiting the scope thereof.

EXAMPLES

Each of the tests described in detail below corresponds to the use of the following bases 2 to 5 and of the following couplers 1 to 4 of the 2-(sulphonylamino)phenol type of formula (I):

Coupler 1: N-(2-hydroxy-4-methylphenyl)methanesulphonamide;
Coupler 2: N-(4-amino-2-hydroxyphenyl)methanesulphonamide;
Coupler 3: N-(4-amino-2-hydroxyphenyl)benzenesulphonamide;
Coupler 4: N-(2-hydroxy-4-methylphenyl)benzenesulphonamide.

Base 1: para-phenylenediamine;
Base 2: para-aminophenol;
Base 3: 4,5-diamino-1-ethyl-3-methylpyrazole.2HCl;
Base 4: 3,7-diaminopyrazolo[1,5-a]pyrimidine.2HCl;
Base 5: N,N-bis(hydroxyethyl)-para-phenylenediamine sulphate.

Dyeing compositions are prepared from these bases and couplers, which compositions comprise (content in grams):

| Coupler | (*) |
|---|---|
| Base | (*) |
| Alkyl ($C_8/C_{10}$ 50/50) polyglucoside as a buffered 60% aqueous solution | 5.4 g |
| Ethyl alcohol, 96°, denatured | 18 g |
| Benzyl alcohol | 1.8 g |
| Polyethylene glycol (8 EO) | 2.7 g |
| Diethylenetriaminepentaacetic acid, pentasodium salt, as a 40% aqueous solution | 1.08 g |
| Sodium metabisulphite powder | 0.585 g |
| Aqueous ammonia | 10 g |
| Demineralized water | q.s. for 100 g |

(*)The amounts of coupler and of base used are shown in the tables below:

| Examples | 1 | 2 | 3 | 4 | 5 |
|---|---|---|---|---|---|
| Coupler 1 | 0.603 g | 0.603 g | 0.603 g | 0.603 g | 0.603 g |
| Base 1 | 0.32 g | — | — | — | — |
| Base 2 | — | 0.33 g | — | — | — |
| Base 3 | — | — | 0.63 g | — | — |
| Base 4 | — | — | — | 0.66 g | — |
| Base 5 | — | — | — | — | 0.89 g |

| Examples | 6 | 7 | 8 | 9 | 10 |
|---|---|---|---|---|---|
| Coupler 2 | 0.89 g | 0.89 g | 0.89 g | 0.89 g | 0.89 g |
| Base 1 | 0.32 g | — | — | — | — |
| Base 2 | — | 0.33 g | — | — | — |
| Base 3 | — | — | 0.63 g | — | — |
| Base 4 | — | — | — | 0.66 g | — |
| Base 5 | — | — | — | — | 0.89 g |

| Examples | 11 | 12 | 13 | 14 | 15 |
|---|---|---|---|---|---|
| Coupler 3 | 0.79 g | 0.79 g | 0.79 g | 0.79 g | 0.79 g |
| Base 1 | 0.32 g | — | — | — | — |
| Base 2 | — | 0.33 g | — | — | — |
| Base 3 | — | — | 0.63 g | — | — |
| Base 4 | — | — | — | 0.6 g | — |
| Base 5 | — | — | — | — | 0.89 g |

| Examples | 16 | 17 | 18 | 19 | 20 |
|---|---|---|---|---|---|
| Coupler 4 | 0.78 g | 0.78 g | 0.78 g | 0.78 g | 0.78 g |
| Base 1 | 0.32 g | — | — | — | — |
| Base 2 | — | 0.33 g | — | — | — |
| Base 3 | — | — | 0.63 g | — | — |
| Base 4 | — | — | — | 0.66 g | — |
| Base 5 | — | — | — | — | 0.89 g |

Each of the dyeing compositions thus obtained was mixed with an equal amount of an oxidizing composition consisting of a 20-volume hydrogen peroxide solution (6 by weight) exhibiting a pH of approximately 3.

Each mixture thus obtained exhibited a pH of approximately 9.5 and was applied for 30 minutes to locks of natural grey hair comprising 90% white hairs. The locks of hair were subsequently rinsed, washed with a standard shampoo and then dried.

The level of tone and the highlights of the colouring obtained were subsequently determined. The following results are then obtained:

| Examples | Coupler | Base | Highlights and level of tone |
|---|---|---|---|
| 1 | Coupler 1 | Base 1 | Ash dark blond |
| 2 | | Base 2 | Ash golden very light blond |
| 3 | | Base 3 | Ash iridescent very light blond |
| 4 | | Base 4 | Deep purple dark blond |
| 5 | | Base 5 | Blueish green blond |
| 6 | Coupler 2 | Base 1 | Ash mahogany dark blond |
| 7 | | Base 2 | Ash golden very light blond |
| 8 | | Base 3 | Ash red dark blond |
| 9 | | Base 4 | Pearlescent ash very light blond |
| 10 | | Base 5 | Intense ash light chestnut |
| 11 | Coupler 3 | Base 1 | Pearlescent mahogany dark blond |
| 12 | | Base 2 | Ash pearlescent coppery blond |
| 13 | | Base 3 | Red pearlescent blond |
| 14 | | Base 4 | Red mahogany dark blond |
| 15 | | Base 5 | Matt blue ash blend |
| 16 | Coupler 4 | Base 1 | Matt ash dark blond |
| 17 | | Base 2 | Pearlescent golden blond |
| 18 | | Base 3 | Ash mahogany very light blond |
| 19 | | Base 4 | Deep purple light chestnut |
| 20 | | Base 5 | Blueish green light chestnut |

What is claimed is:
1. Composition for the oxidation dyeing of keratinous fibres, comprising, in a medium appropriate for the dyeing of the said fibres:
   at least one oxidation base;
   and at least one coupler chosen from the compounds of following formula (I) and/or their addition salts with an acid:

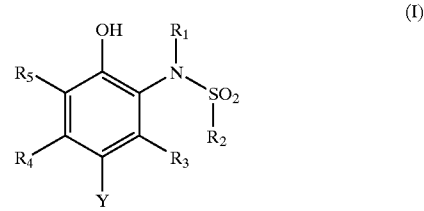

(I)

in which:
   $R_1$ represents a hydrogen atom or a linear or branched radical comprising from 1 to 15 carbon atoms, said branching or branchings optionally forming one or more carbonaceous rings comprising from 3 to 7 ring members, which can comprise one or more double bonds and/or one or more triple bonds, said double bonds optionally resulting in aromatic groups, and one or more carbon atoms of which can be replaced by an oxygen, nitrogen or sulphur atom or by an $SO_2$ group and the carbon atoms of which can, independently of one another, be substituted by one or more halogen atoms, the said $R_1$ radical comprising neither peroxide bonds nor diazo, nitro and nitroso radicals;
   $R_2$ represents a hydrogen atom or a linear or branched radical comprising from 1 to 20 carbon atoms, said branching or branchings optionally forming one or more carbonaceous rings comprising from 3 to 7 ring members, which can comprise one or more double bonds and/or one or more triple bonds, said double bonds optionally resulting in aromatic groups, and one or more carbon atoms of which can be replaced by an oxygen, nitrogen or sulphur atom or by an $SO_2$ group and the carbon atoms of which can, independently of one another, be substituted by one or more halogen atoms, the said $R_2$ radical comprising neither peroxide bonds nor diazo, nitro and nitroso radicals;

$R_3$, $R_4$ and $R_5$, which are identical or different, represent a hydrogen or halogen atom or a linear or branched radical comprising from 1 to 20 carbon atoms, said branching or branchings optionally forming one or more rings comprising from 3 to 7 ring members, which can comprise one or more double bonds and/or one or more triple bonds, said double bonds optionally resulting in aromatic groups, and one or more carbon atoms of which can be replaced by an oxygen, nitrogen or sulphur atom or by an $SO_2$ group and the carbon atoms of which can, independently of one another, be substituted by one or more halogen atoms, the said radical comprising neither peroxide bonds nor diazo, nitro and nitroso radicals and it being understood that $R_5$ cannot represent a hydroxyl, thio or amino radical and it being understood that the $R_3$, $R_4$ and $R_5$ radicals cannot be connected to the benzene ring of the formula (I) via an —NH—NH— bond;

Y represents a hydrogen or halogen atom; an —$OR_6$, —$SR_6$ or —NH—$SO_2R_6$ group in which $R_6$ represents a linear or branched $C_1$–$C_6$ alkyl radical, said branching or branchings optionally forming one or more rings comprising from 3 to 6 ring members, optionally substituted by one or more radicals chosen from the group: halogen, hydroxyl, $C_1$–$C_4$ alkoxy, amino or $C_1$–$C_4$ aminoalkyl; a phenyl radical, optionally substituted by one or two radicals chosen from the group: $C_1$–$C_4$ alkyl, trifluoromethyl, carboxyl, $C_1$–$C_4$ alkoxycarbonyl, halogen, hydroxyl, $C_1$–$C_4$ alkoxy, amino or $C_1$–$C_4$ amino-alkyl; or a benzyl radical.

2. Composition according to claim 1, wherein $R_1$ denotes a hydrogen atom; an $A_1$ group composed of a linear or branched $C_1$–$C_8$ alkyl radical which can carry one or two double bonds or one triple bond, which may or may not be substituted by a group chosen from an $A_2$, $A_4$ and $A_5$ group as defined below, which may or may not be substituted by one or two identical or different groups chosen from the N—($C_1$–$C_3$)alkylamino, N—($C_1$–$C_3$)-alkyl-N—($C_1$–$C_3$)alkylamino, ($C_1$–$C_6$)alkoxy, oxo, alkoxy-carbonyl, acyloxy, amido, acylamino, ureyl, sulphoxy, sulphonyl, sulphonamido, sulphonylamino, bromo, cyano or carboxyl groups, and which may or may not be substituted by one or more hydroxyl, fluoro or chloro groups; an $A_2$ group composed of an aromatic group of phenyl or naphthyl type which may or may not be substituted by one to three identical or different groups chosen from the methyl, trifluoromethyl, ethyl, isopropyl, butyl, pentyl, fluoro, chloro, bromo, methoxy, trifluoromethoxy, ethoxy, propyloxy, acetyl-oxy, acetyl and cyano groups; an $A_3$ group composed of heteroaromatic groups chosen from the furanyl, thio-phenyl, pyrrolyl, imidazolyl, thiazolyl, oxazolyl, 1,2,3-triazolyl, 1,2,4-triazolyl, isoxazolyl, iso-thiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolinyl, benzimidazolyl or benzopyrimidyl groups, optionally substituted by 1 to 3 radicals chosen from linear or branched $C_1$–$C_4$ alkyl, $C_1$–$C_4$ (poly)hydroxyalkyl, carboxyl, alkoxycarbonyl, halogen, amido, amino or hydroxyl; an $A_4$ group composed of a $C_3$–$C_7$ cycloalkyl radical or a norbornanyl radical optionally carrying a double bond and optionally substituted by 1 or 2 radicals defined by linear or branched $C_1$–$C_4$ alkyl, $C_1$–$C_4$ (poly)hydroxyalkyl, carboxyl, alkoxycarbonyl, halogen, amido, amino or hydroxyl; or an $A_5$ group corn-posed of a heterocycle chosen from the dihydrofuranyl, tetrahydrofuranyl, butyrolactoneyl, dihydrothiophenyl, tetrahydrothiophenyl, tetrahydrothiophenoneyl, imino-thiolanyl, dihydropyrrolyl, pyrrolidinyl, pyrroli-dinoneyl, imidazolidinoneyl, imidazolidinethioneyl, oxazolidinyl, oxazolidinoneyl, oxazolanethioneyl, thiazolidinyl, isothiazoloneyl, mercaptothiazolinyl, pyrazolidinoneyl, iminothiolanyl, dioxolanyl, penta-lactoneyl, dioxanyl, dihydropyridinyl, piperidinyl, pentalactamyl, morpholinyl, pyrazoli(di)nyl, pyrimi(di)nyl, pyrazinyl, piperazinyl and azepinyl rings.

3. Composition according to claim 2, wherein $R_1$ represents a hydrogen atom, a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxy-benzyl, (trifluoromethoxy)benzyl, 3,4-methylenedioxy-benzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; or a 2-hydroxyethyl, 2-methoxyethyl or 2-ethoxyethyl group.

4. Composition according to claim 1, characterized in that, in the said compounds of formula (I), $R_2$ denotes a hydrogen atom; an amino group; or an $A_1$ group composed of a linear or branched $C_1$–$C_8$ alkyl radical which can carry one or two double bonds or one triple bond, which may or may not be substituted by a group chosen from an $A_2$, $A_4$ and $A_5$ group as defined below, which may or may not be substituted by one or two identical or different groups chosen from the N—($C_1$–$C_3$)alkylamino, N—($C_1$–$C_3$)-alkyl-N—($C_1$–$C_3$)alkylamino, ($C_1$–$C_6$)alkoxy, oxo, alkoxy-carbonyl, acyloxy, amido, acylamino, ureyl, sulphoxy, sulphonyl, sulphonamido, sulphonylamino, bromo, cyano or carboxyl groups, and which may or may not be substituted by one or more hydroxyl, fluoro or chloro groups; an $A_2$ group composed of an aromatic group of phenyl or naphthyl type which may or may not be substituted by one to three identical or different groups chosen from the methyl, trifluoromethyl, ethyl, isopropyl, butyl, pentyl, fluoro, chloro, bromo, methoxy, trifluoromethoxy, ethoxy, propyloxy, acetyl-oxy, acetyl and cyano groups; an $A_3$ group composed of heteroaromatic groups chosen from the furanyl, thio-phenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolinyl, benzimidazolyl or benzopyrimidyl groups, optionally substituted by 1 to 3 radicals chosen from linear or branched $C_1$–$C_4$ alkyl, $C_1$–$C_4$ (poly)hydroxyalkyl, carboxyl, alkoxycarbonyl, halogen, amido, amino or hydroxyl; an $A_4$ group composed of a $C_3$–$C_7$ cycloalkyl radical or a norbornanyl radical optionally carrying a double bond and optionally substituted by 1 or 2 radicals defined by linear or branched $C_1$–$C_4$ alkyl, $C_1$–$C_4$ (poly)hydroxyalkyl, carboxyl, alkoxycarbonyl, halogen, amido, amino or hydroxyl; or an $A_5$ group composed of a heterocycle chosen from the dihydrofuranyl, tetrahydrofuranyl, butyrolactoneyl, dihydrothiophenyl, tetrahydrothiophenyl, tetrahydrothiophenoneyl, imino-thiolanyl, dihydropyrrolyl, pyrrolidinyl, pyrroli-dinoneyl, imidazolidinoneyl, imidazolidinethioneyl, oxazolidinyl, oxazolidinoneyl, oxazolanethioneyl, thiazolidinyl, isothiazoloneyl, mercaptothiazolinyl, pyrazolidinoneyl, iminothiolanyl, dioxolanyl, penta-lactoneyl, dioxanyl, dihydropyridinyl, piperidinyl, pentalactamyl, morpholinyl, pyrazoli(di)nyl, pyrimi(di)nyl, pyrazinyl, piperazinyl and azepinyl rings; the said $A_1$, $A_2$, $A_3$, $A_4$ or $A_5$ groups optionally being separated from the sulphur, situated in the 8 position, of the sulphonamide functional group of the said compound of formula (I) by an —NH— or —N—($C_1$–$C_3$) alkyl-group.

5. Composition according to claim 4, wherein $R_2$ denotes a radical chosen from the group (G1) consisting of a methyl, trifluoromethyl, ethyl, 2-chloroethyl, propyl, 3-chloropropyl, isopropyl, butyl, phenyl, ethoxy, amino and dimethylamino radical.

6. Composition according to claim 1, characterized in that, in the said compounds of formula (I), $R_3$ and $R_4$, which are identical or different, denote a hydrogen or halogen atom; a hydroxyl or amino group; an $A_1$, $A_4$ or $A_5$ group; or an $A_1$, $A_2$, $A_3$, $A_4$ or $A_5$ group which is separated from the phenol nucleus of the said formula (I) by an oxygen atom or by an —NH—, —N—($C_1$–$C_3$)alkyl-, —O(O)—, —NH(CO)—, —N—($C_1$–$C_3$)alkyl(CO)—, —NH[C=NH]—, —NH(CO)NH—, —NH(CO)N—($C_1$–$C_3$)alkyl-, —NH(CO)O—, —NHSO$_2$, —NHSO$_2$ NH— or —NHSO$_2$ N—($C_1$–$C_3$)alkyl-group said $A_1$ group being composed of a linear or branched $C_1$–$C_8$ alkyl radical which can carry one or two double bonds or one triple bond, which may or may not be substituted by a group chosen from an $A_2$, $A_4$ and $A_5$ group as defined below, which may or may not be substituted by one or two identical or different groups chosen from the N—($C_1$–$C_3$)alkylamino, N—($C_1$–$C_3$)-alkyl-N—($C_1$–$C_3$)alkylamino, ($C_1$–$C_6$)alkoxy, oxo, alkoxy-carbonyl, acyloxy, amido, acylamino, ureyl, sulphoxy, sulphonyl, sulphonamido, sulphonylamino, bromo, cyano or carboxyl groups, and which may or may not be substituted by one or more hydroxyl, fluoro or chloro groups; said $A_2$ group being composed of an aromatic group of phenyl or naphthyl type which may or may not be substituted by one to three identical or different groups chosen from the methyl, trifluoromethyl, ethyl, isopropyl, butyl, pentyl, fluoro, chloro, bromo, methoxy, trifluoromethoxy, ethoxy, propyloxy, acetyl-oxy, acetyl and cyano groups; said $A_3$ group being composed of heteroaromatic groups chosen from the furanyl, thio-phenyl, pyrrolyl, imidazolyl, thiazolyl, oxazolyl, 1 2,3-triazolyl, 1,2,4-triazolyl, isoxazolyl, iso-thiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolinyl, benzimidazolyl or benzopyrimidyl groups, optionally substituted by 1 to 3 radicals chosen from linear or branched $C_1$–$C_4$ alkyl, $C_1$–$C_4$ (poly)hydroxyalkyl, carboxyl, alkoxycarbonyl, halogen, amido, amino or hydroxyl; said $A_4$ group being composed of a $C_3$–$C_7$ cycloalkyl radical or a norbornanyl radical optionally carrying a double bond and optionally substituted by 1 or 2 radicals defined by linear or branched $C_1$–$C_4$ alkyl, $C_1$–$C_4$ (poly)hydroxyalkyl, carboxyl, alkoxycarbonyl, halogen, amido, amino or hydroxyl; and said $A_5$ group being composed of a heterocycle chosen from the dihydrofuranyl, tetrahydrofuranyl, butyrolactoneyl, dihydrothiophenyl, tetrahydrothiophenyl, tetrahydrothiophenoneyl, imino-thiolanyl, dihydropyrrolyl, pyrrolidinyl, pyrroli-dinoneyl, imidazolidinoneyl, imidazolidinethioneyl, oxazolidinyl, oxazolidinoneyl, oxazolanethioneyl, thiazolidinyl, isothiazoloneyl, mercaptothiazolinyl, pyrazolidinoneyl, iminothiolanyl, dioxolanyl, penta-lactoneyl, dioxanyl, dihydropyridinyl, piperidinyl, pentalactamyl, morpholinyl, pyrazoli(di)nyl, pyrimi(di)nyl, pyrazinyl, piperazinyl and azepinyl rings.

7. Composition according to claim 6, characterized in that $R_3$ represents a hydrogen or chlorine atom; a methyl, hydroxymethyl, methoxymethyl, 1-hydroxyethyl, aminomethyl or methylaminomethyl radical; a hydroxyl, methoxy or acetoxy radical; an amino, methylamino or 2-hydroxyethylamino radical; an —NH(CO)$R_7$ group in which $R_7$ represents a radical chosen from the group (G2) consisting of the methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethyl-phenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4-di-methoxybenzyl, 4-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)-methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethyl-isoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, hepta-fluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)-ethyl, 1-phenoxyethyl, 1-acetoxyethyl, methoxy-carbonyl, ethoxycarbonyl, (methoxycarbonyl)methyl, 2-carboxyethyl, 2-(methoxycarbonyl)ethyl, 2-carboxy-cyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromo-phenoxy, 4-chlorophenoxy, 4-methoxyphenoxy, naphth-2-yloxy, benzyloxy; amino, methylamino, ethylamino, propylamino, isopropylamino, butylamino, cyclohexyl-amino, allylamino, 2-chloroethylamino, 3-chloropropyl-amino, carboxymethylamino, phenylamino, fluorophenyl-amino, (trifluoromethyl)phenylamino, chlorophenyl-amino, bromophenylamino, 4-acetylphenylamino, methoxy-phenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or an —NHSO$_2$R$_8$ group in which R$_8$ represents a radical chosen from the group (G1) consisting of a methyl, trifluoromethyl, ethyl, 2-chloroethyl, propyl, 3-chloropropyl, isopropyl, butyl, phenyl, ethoxy, amino and dimethylamino radical.

8. Composition according to claim 6, characterized in that R$_4$ represents a hydrogen or chlorine atom; a methyl, ethyl, hydroxymethyl, methoxymethyl, amino-methyl or methylaminomethyl radical; a hydroxyl, methoxy, acetoxy, amino, methylamino, N-piperidino or N-morpholino group; an —NH(CO)R$_{10}$ group in which R$_{10}$ represents one of the radicals chosen from the group (G2) consisting of the methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethyl-phenyl, 2,4,6-trimethylphenyl, 4-ethylphenyl, (tri-fluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chloro-phenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-di-methoxybenzyl, 4'-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)-methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethyl-isoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, hepta-fluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)-ethyl, 1-phenoxyethyl, 1-acetoxyethyl, methoxy-carbonyl, ethoxycarbonyl, (methoxycarbonyl)methyl, 2-carboxyethyl, 2-(methoxycarbonyl)ethyl, 2-carboxy-cyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromo-phenoxy, 4-chlorophenoxy, 4-methoxyphenoxy, naphth-2-yloxy, benzyloxy; amino, methylamino, ethylamino, propylamino, isopropylamino, butylamino, cyclohexyl-amino, allylamino, 2-chloroethylamino, 3-chloropropyl-amino, carboxymethylamino, phenylamino, fluorophenyl-amino, (trifluoromethyl)phenylamino, chlorophenyl-amino, bromophenylamino, 4-acetylphenylamino, methoxy-phenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or an —NHSO$_2$R$_{11}$ group in which R$_{11}$ represents one of the radicals chosen from the group (G1) consisting of a methyl, trifluoromethyl, ethyl, 2-chloroethyl, propyl, 3-chloropropyl, isopropyl, butyl, phenyl, ethoxy, amino and dimethylamino radical.

9. Composition according to claim 1, characterized in that, in the said compounds of formula (I), R$_5$ denotes a hydrogen or halogen atom; an A$_1$, A$_4$ or A$_5$ group or an A$_1$, A$_2$, A$_3$, A$_4$ or A$_5$ group which is separated from the phenyl nucleus of the compounds of formula (I) by an oxygen or sulphur atom or by an —NH—, —N—(C$_1$–C$_3$)alkyl-, —NH (CO)—, —N—(C$_1$–C$_3$)alkyl(CO)—, —NH[C=NH]—, —NH(CO)NH—, —NH(CO)N—(C$_1$–C$_3$)alkyl- or —NH (CO)O-group; wherein said A$_1$ group is composed of a linear or branched C$_1$–C$_8$ alkyl radical which can carry one or two double bonds or one triple bond, which may or may not be substituted by a group chosen from an A$_2$, A$_4$ and A$_5$ group as defined below, which may or may not be substituted by one or two identical or different groups chosen from the N—(C$_1$–C$_3$)alkylamino, N—(C$_1$–C$_3$)-alkyl-N—(C$_1$–C$_3$)alkylamino, (C$_1$–C$_6$)alkoxy, oxo, alkoxy-carbonyl, acyloxy, amido, acylamino, ureyl, sulphoxy, sulphonyl, sulphonamido, sulphonylamino, bromo, cyano or carboxyl groups, and which may or may not be substituted by one or more hydroxyl, fluoro or chloro groups; said A$_2$ group being composed of an aromatic group of phenyl or naphthyl type which may or may not be substituted by one to three identical or different groups chosen from the methyl, trifluoromethyl, ethyl, isopropyl, butyl, pentyl, fluoro, chloro, bromo, methoxy, trifluoromethoxy, ethoxy, propyloxy, acetyl-oxy, acetyl and cyano groups; said A$_3$ group composed of heteroaromatic groups chosen from the furanyl, thio-phenyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazolo-imidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolinyl, benzimidazolyl or benzopyrimidyl groups, optionally substituted by 1 to 3 radicals chosen from linear or branched C$_1$–C$_4$ alkyl, C$_1$–C$_4$ (poly) hydroxyalkyl, carboxyl, alkoxycarbonyl, halogen, amido, amino or hydroxyl; said A$_4$ group being composed of a cycloalkyl radical or a norbornanyl radical optionally carrying a double bond and optionally substituted by 1 or 2 radicals defined by linear or branched C$_1$–C$_4$ alkyl, C$_1$–C$_4$ (poly)hydroxyalkyl, carboxyl, alkoxycarbonyl, halogen, amido, amino or hydroxyl; and said A$_5$ group being composed of a heterocycle chosen from the dihydrofuranyl, tetrahydrofuranyl, butyrolactoneyl, dihydrothiophenyl, tetrahydrothiophenyl, tetrahydrothiophenoneyl, iminothiolanyl, dihydropyrrolyl, pyrrolidinyl, pyrroli-dinoneyl, imidazolidinoneyl, imidazolidinethioneyl, oxazolidinyl, oxazolidinoneyl, oxazolanethioneyl, thiazolidinyl, isothiazoloneyl, mercaptothiazolinyl, pyrazolidinoneyl, iminothiolanyl, dioxolanyl, penta-lactoneyl, dioxanyl, dihydropyridinyl, piperidinyl, pentalactamyl, morpholinyl, pyrazoli(di)nyl, pyrimi(di)nyl, pyrazinyl, piperazinyl and azepinyl rings.

10. Composition according to claim 9, characterized in that R$_5$ represents a hydrogen, chlorine, fluorine or bromine atom; a methyl, trifluoromethyl, allyl, hydroxymethyl, methoxymethyl, 1-hydroxyethyl, aminomethyl, methylaminomethyl, methoxy, acetoxy or methylamino radical; an —NH(CO)R$_{13}$ group in which R$_{13}$ represents one of the radicals (G2) chosen from the group consisting of the methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethyl-phenyl, 2,4,6-trimethylphenyl, 4-ethylphenyl, (tri-fluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chloro-phenyl, dichlorophenyl, bromophenyl, naphth-1-yl, naphth-2-yl, (2-methoxy)naphth-1-yl, benzyl, 4'-methoxybenzyl, 2',5'-dimethoxybenzyl, 3',4'-di-methoxybenzyl, 4-fluorobenzyl, 4'-chlorobenzyl, phenethyl, 2-phenylvinyl, (1-naphthyl)methyl, (2-naphthyl)methyl; tetrahydrofuran-2-yl, furan-2-yl, 5-methyl-2-(trifluoromethyl)furan-3-yl, 2-methyl-5-phenylfuran-3-yl, thiophen-2-yl, (thiophen-2-yl)-methyl, 3-chlorothiophen-2-yl, 2,5-dichlorothiophen-3-yl, benzothiophen-2-yl, 3-chlorobenzothiophen-2-yl, isoxazol-5-yl, 5-methylisoxazol-3-yl, 3,5-dimethyl-isoxazol-4-yl, 1,3-dimethylpyrazol-5-yl, 1-ethyl-3-methylpyrazol-5-yl, 1-tert-butyl-3-methylpyrazol-5-yl, 3-tert-butyl-1-methylpyrazol-5-yl, 4-bromo-1-ethyl-3-methylpyrazol-5-yl, indol-3-ylcarboxyl, pyridinyl, chloropyridinyl, dichloropyridinyl, 5-(bromo)pyridin-3-yl, piperazin-2-yl, quinoxal-2-yl; fluoromethyl, difluoromethyl, trifluoromethyl, 1,1,2,2-tetrafluoroethyl, pentafluoroethyl, hepta-fluoropropyl, 1,1,2,2,3,3,4,4-octafluorobutyl, nona-fluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxy-methyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)-ethyl, 1-phenoxyethyl, 1-acetoxyethyl, methoxy-carbonyl, ethoxycarbonyl, (methoxycarbonyl)methyl, 2-carboxyethyl, 2-(methoxycarbonyl)ethyl, 2-carboxy-cyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromo-phenoxy, 4-chlorophenoxy, 4-methoxyphenoxy, naphth-2-yloxy, benzyloxy; amino, methylamino, ethylamino, propylamino, isopropylamino, butylamino, cyclohexyl-amino, allylamino, 2-chloroethylamino, 3-chloropropyl-amino, carboxymethylamino, phenylamino, fluorophenyl-amino, (trifluoromethyl)phenylamino, chlorophenyl-amino, bromophenylamino, 4-acetylphenylamino, methoxy-phenylamino, (trifluoromethoxy)phenylamino, naphth-1-ylamino, benzylamino, phenethylamino, pyrid-3-ylamino, dimethylamino, 1-pyrrolidinyl and 4-morpholinyl radicals; or an —NHSO$_2$ R$_{14}$ group in which R$_{14}$ represents one of the radicals (G1) chosen from the group consisting of a methyl, trifluoromethyl, ethyl, 2-chloroethyl, propyl, 3-chloropropyl, isopropyl, butyl, phenyl, ethoxy, amino and dimethylamino radical.

11. Composition according to claim 1, characterized in that, in the said compounds of formula (I), Y denotes a hydrogen, chlorine, fluorine or bromine atom; a methoxy, ethoxy, propoxy, benzyloxy or phenoxy group; or an —OCH$_2$CH$_2$OCH$_3$, —OCH$_2$CH$_2$OCH$_3$, —OCH$_2$CH$_2$N(CH$_3$)$_2$, —OCH$_2$(CO)OH, —OCH$_2$(CO)OCH$_3$, —OCH$_2$(CO)OC$_2$H$_5$, —SCH$_2$CH$_2$CO$_2$H or —NHSO$_2$ CH$_3$ group.

12. Composition according to claim 1, characterized in that the compounds of formula (I) are chosen from those in which:

i) R$_1$ represents a hydrogen atom;
R$_2$ represents a methyl, ethyl, phenyl or dimethylamino radical;
R$_3$ represents a hydroxyl, amino or methylamino radical; an —NH(CO)R$_{16}$ group in which R$_{16}$ represents a radical chosen from the group (G4) consisting of the methyl, methoxymethyl, 2-carboxyethyl, methoxy, amino, ethylamino and 1-pyrrolidinyl radicals; methanesulphonylamino, ethanesulphonylamino and dimethylaminosulphonylamino;
R$_4$ represents a hydrogen or chlorine atom or a methyl group;
R$_5$ represents a hydrogen, chlorine or fluorine atom or a methyl group;
Y represents a hydrogen or chlorine atom or a methoxy or —OCH$_2$(CO)OCH$_3$ group;

ii) R$_1$ represents a hydrogen atom;
R$_2$ represents a methyl, ethyl, phenyl or dimethyl-amino radical;
R$_3$ represents a hydrogen atom or a methyl radical;
R$_4$ represents a hydroxyl, amino, methylamino or —NH(CO)R$_{17}$ group in which R$_{17}$ represents one of the radicals listed in the group (G4) defined above; or a methanesulphonylamino, ethanesulphonylamino or dimethylaminosulphonylamino group;
R$_5$ represents a hydrogen, chlorine or fluorine atom or a methyl, methoxy or methylamino group;
Y represents a hydrogen or chlorine atom or a methoxy or —OCH$_2$(CO)OCH$_3$ group;

iii) R$_1$ represents a hydrogen atom;
R$_2$ represents a methyl, ethyl, phenyl or dimethyl-amino radical;
R$_3$ represents a hydrogen atom or a methyl radical;
R$_4$ represents a hydrogen or chlorine atom or a methyl, methoxy or methylamino radical;
R$_5$ represents a methylamino or —NH(CO)R$_{18}$ group in which R$_{18}$ represents one of the radicals listed in the group (G4) defined above; or a methanesulphonylamino, ethanesulphonylamino or dimethylaminosulphonylamino group;
Y represents a hydrogen or chlorine atom or a methoxy or —OCH$_2$(CO)OCH$_3$ group;

iv) R$_1$ represents a hydrogen atom;
R$_2$ represents a methyl, ethyl, phenyl or dimethylamino radical;
R$_3$ represents a hydrogen atom or a methyl radical;
R$_4$ represents a hydrogen or chlorine atom or a methyl radical;
R$_5$ represents a hydrogen, chlorine or fluorine atom or a methyl radical;
Y represents a hydrogen or chlorine atom or a methoxy or —OCH$_2$(CO)OCH$_3$ group.

13. Composition according to claim 1, characterized in that the compounds of formula (I) are chosen from:
N-(2-hydroxyphenyl)methanesulphonamide;
N-(2-hydroxy-4-methylphenyl)methanesulphonamide;
N-(2-hydroxy-4-aminophenyl)methanesulphonamide;
N-(2-hydroxy-4-(acetylamino)phenyl)methane-sulphonamide;
N-(2-hydroxy-4-(methoxycarbonylamino)phenyl)-methanesulphonamide;
N-(2-hydroxy-5-chlorophenyl)methanesulphonamide;
N-(2-hydroxy-4-methyl-5-chlorophenyl)methanesulphonamide;
N-(2-hydroxy-4-amino-5-chlorophenyl)methanesulphonamide;

N-(2-hydroxy-4-acetylamino-5-chlorophenyl)-methanesulphonamide;
N-(2-hydroxy-4-methoxycarbonylamino-5-chlorophenyl)methanesulphonamide;
N-(2-hydroxy-5-methoxyphenyl)methanesulphonamide;
N-(2-hydroxy-4-methyl-5-methoxyphenyl)methanesulphonamide;
N-(2-hydroxy-4-amino-5-methoxyphenyl)methanesulphonamide;
N-(2-hydroxy-4-acetylamino-5-methoxyphenyl)-methanesulphonamide;
N-(2-hydroxy-4-methoxycarbonylamino-5-methoxyphenyl)methanesulphonamide;
N-(2-hydroxy-6-aminophenyl)methanesulphonamide;
N-(2-hydroxy-6-(acetylamino)phenyl)methanesulphonamide;
N-(2-hydroxy-4,6-diaminophenyl)methanesulphonamide;
N-(2-hydroxy-4-acetylamino-6-aminophenyl)methanesulphonamide;
N-(2-hydroxy-3,5-dichloro-4-methylphenyl)methanesulphonamide;
N-(2-hydroxy-3,5-dichloro-4-aminophenyl)methanesulphonamide;
N-(2-hydroxy-3,5-dichloro-4-(acetylamino)phenyl)-methanesulphonamide;
N-(2-hydroxy-3,5-dichloro-4-(methoxycarbonyl-amino)phenyl)methanesulphonamide;
N-(2-hydroxy-3-(methanesulphonylamino)phenyl)-methanesulphonamide;
N-(2-hydroxyphenyl)benzenesulphonamide;
N-(2-hydroxy-4-methylphenyl)benzenesulphonamide;
N-(2-hydroxy-4-aminophenyl)benzenesulphonamide;
N-(2-hydroxy-4-(acetylamino)phenyl)benzenesulphonamide;
N-(2-hydroxy-4-(methoxycarbonylamino)phenyl)-benzenesulphonamide;
N-(2-hydroxy-5-chlorophenyl)benzenesulphonamide;
N-(2-hydroxy-4-methyl-5-chlorophenyl)benzenesulphonamide;
N-(2-hydroxy-4-amino-5-chlorophenyl)benzenesulphonamide;
N-(2-hydroxy-4-acetylamino-5-chlorophenyl)benzenesulphonamide;
N-(2-hydroxy-4-methoxycarbonylamino-5-chlorophenyl)benzenesulphonamide;
N-(2-hydroxy-5-methoxyphenyl)benzenesulphonamide;
N-(2-hydroxy-4-methyl-5-methoxyphenyl)benzenesulphonamide;
N-(2-hydroxy-4-amino-5-methoxyphenyl)benzenesulphonamide;
N-(2-hydroxy-4-acetylamino-5-methoxyphenyl)-benzenesulphonamide;
N-(2-hydroxy-4-methoxycarbonylamino-5-methoxyphenyl)benzenesulphonamide;
N-(2-hydroxy-6-aminophenyl)benzenesulphonamide;
N-(2-hydroxy-6-(acetylamino)phenyl)benzenesulphonamide;
N-(2-hydroxy-4,6-diaminophenyl)benzenesulphonamide;
N-(2-hydroxy-4-acetylamino-6-aminophenyl)benzenesulphonamide;
N-(2-hydroxy-3,5-dichloro-4-methylphenyl)benzenesulphonamide;
N-(2-hydroxy-3,5-dichloro-4-aminophenyl)benzenesulphonamide;
N-(2-hydroxy-3,5-dichloro-4-(acetylamino)phenyl)benzene-sulphonamide;
N-(2-hydroxy-3,5-dichloro-4-(methoxycarbonyl-amino)phenyl)benzenesulphonamide;
N-(2-hydroxy-3-(benzenesulphonylamino)phenyl)-benzenesulphonamide; and their addition salts with an acid.

14. Composition according to claim 1, characterized in that the compound or compounds of formula (I) and/or the addition salt or their addition salts with an acid preferably represent from 0.0005 to 12% by weight approximately of the total weight of the dyeing composition.

15. Composition according to claim 1, characterized in that the addition salts with an acid are chosen from hydrochlorides, hydrobromides, sulphates, citrates, succinates, tartrates, lactates and acetates.

16. Process for the dyeing of keratinous fibres and in particular of human keratinous fibres, such as the hair, characterized in that at least one dyeing composition as defined in claim 1 is applied to the said fibres and in that the colour is developed at acidic, neutral or alkaline pH using an oxidizing agent which is added only at the time of use to the dyeing composition or which is present in an oxidizing composition applied simultaneously or sequentially in a separate fashion.

17. Process according to claim 16, wherein the oxidizing agent is chosen from hydrogen peroxide, urea hydrogen peroxide, alkali metal bromates, persalts and enzymes.

18. Process according to claim 17, wherein the enzymes are chosen from peroxidases, laccases, tyrosinases and oxidoreductases.

19. Multi-compartment device or multi-compartment dyeing kit, a first compartment of which includes a dyeing composition as defined in claim 1 and a second compartment of which includes an oxidizing composition.

* * * * *